(12) United States Patent
Offermans et al.

(10) Patent No.: US 8,525,129 B2
(45) Date of Patent: Sep. 3, 2013

(54) GAS SENSING DEVICE

(75) Inventors: Peter Offermans, Eindhoven (NL); Mercedes Crego Calama, Geldrop-Mierlo (NL)

(73) Assignee: Stichting IMEC Nederland, Eindhoven (NL)

( * ) Notice: Subject to any disclaimer, the term of this patent is extended or adjusted under 35 U.S.C. 154(b) by 355 days.

(21) Appl. No.: 12/743,909

(22) PCT Filed: Dec. 17, 2008

(86) PCT No.: PCT/EP2008/067729
§ 371 (c)(1),
(2), (4) Date: Jul. 1, 2010

(87) PCT Pub. No.: WO2009/077557
PCT Pub. Date: Jun. 25, 2009

(65) Prior Publication Data
US 2010/0264333 A1    Oct. 21, 2010

Related U.S. Application Data

(60) Provisional application No. 61/014,117, filed on Dec. 17, 2007.

(51) Int. Cl.
*G01N 21/64* (2006.01)
*G01N 21/39* (2006.01)

(52) U.S. Cl.
USPC .................. 250/458.1; 250/483.1; 250/484.2; 356/437; 356/445

(58) Field of Classification Search
USPC ................ 250/458.1, 483.1, 484.2; 356/437, 356/445
See application file for complete search history.

(56) References Cited

U.S. PATENT DOCUMENTS

| 5,411,709 A * | 5/1995 | Furuki et al. .................... 422/91 |
| 7,889,113 B2 * | 2/2011 | Cardiasmenos et al. ......... 342/22 |
| 2003/0132392 A1 | 7/2003 | Kuroda et al. |
| 2009/0207413 A1 * | 8/2009 | Carpenter et al. ............. 356/437 |

OTHER PUBLICATIONS

PCT International Search Report and Written Opinion, PCT International Application No. PCT/EP20081067729 dated Apr. 17, 2009.
Komarala, Vamsi K. et al., "Enhanced Forster Resonance Energy Transfer Between the CdTe Quantum Dots in Proximity to Gold Nanoparticles", Proceedings of the SPIE, vol. 6641, Jan. 1, 2007, pp. 66410Y-1 to 66410Y-7.

(Continued)

*Primary Examiner* — Casey Bryant
(74) *Attorney, Agent, or Firm* — McDonnell Boehnen Hulbert & Berghoff LLP

(57) ABSTRACT

The present invention relates to a gas sensing device comprising a nanoparticle layer (1) and a quantum dot layer (3) separated from each other by a gas absorption layer (2) which has a thickness which changes upon absorption of a gas. The nanoparticle layer (1) is provided for generating a surface plasmon resonance within a plasmon resonance frequency range upon illumination with light within a light frequency range; the quantum dot layer (3) has an absorption spectrum overlapping with said plasmon resonance frequency range of said nanoparticle layer (1) and shows photoluminescence in a photoluminescence emission frequency range upon absorption of energy within its absorption spectrum. The present invention further relates to a method for fabricating such a gas sensing device and to a method of using such a gas sensing device.

23 Claims, 7 Drawing Sheets (a)

(b)

(56) References Cited

OTHER PUBLICATIONS

Wargnier, Richard et al., "Energy Transfer in Aqueous Solutions of Oppositely Charged CdSe/ZnS Core/Shell Quantum Dots and in Quantum Dot-Nanogold Assemblies", Nano Letters, American Chem. Society, vol. 4, No. 3, pp. 451-457. Note: Pubisihed 2004.

Cheng, Mu-Tian et al., "Coherent Exciton-Plasmon Interaction in the Hybrid Semiconductor Quantum Dot and Metal Nanoparticle Complex", Optics Letters, vol. 32, No. 15, Aug. 1, 2007, pp. 2125-2127.

Schalkhammer et al., "The Use of Metal-Island-Coated pH-Sensitive Swelling Polymers for Biosensor Applications", Sensors and Actuators B 24-25 (1995), pp. 166-172.

Matsui, Jun et al., "SPR Sensor Chip for Detection of Small Molecules Using Molecularly Imprinted Polymer with Embedded Gold Nanoparticles", Anal. Chem., vol. 77, 2005, pp. 4282-4285.

McCurley, M.F., "An Optical Biosensor Using a Fluorescent, Swelling Sensing Elements", Biosensors & Bioelectronics, vol. 9, 1994, pp. 527-533.

\* cited by examiner (a)

(b)

(a)

(b)

(a)

(b)

GAS SENSING DEVICE

CROSS REFERENCE TO RELATED APPLICATIONS

The present application is a national stage entry of PCT/EP2008/067729, filed Dec. 17, 2008, and claims priority to U.S. Provisional Application 61/014,117, filed Dec. 17, 2007, the entire contents of each of which are incorporated herein by reference.

TECHNICAL FIELD

The present invention relates to a gas sensor, and more specifically to an optical gas sensor. Further, the invention relates to a method of manufacturing a gas sensor and to a method of operating a gas sensor.

BACKGROUND ART

Optical gas sensors have been proposed that make use of the swelling of polymers by measuring the change in optical thickness of the polymer. Several detection techniques have been used such as surface plasmon resonance (Matsui et al. Anal. Chem. 77 4282 (2005)), interference (Schalkhammer et al. Sensors and Actuators B 24 166 (1995)) and fluorescence (McCurley Biosensors & Bioelectronics 9 527 (1994)).

Matsui et al. (Anal. Chem. 77 4282 (2005)) prepared a molecularly imprinted polymer gel with embedded gold nanoparticles on a gold substrate of a chip to obtain surface plasmon resonance (SPR). The sensing is based on swelling of the imprinted polymer gel that is triggered by an analyte binding event within the polymer gel. The swelling causes a greater distance between the gold nanoparticles and the substrate, shifting a dip of the SPR curve to a higher SPR angle. Although the SPR technique can be very sensitive, a disadvantage is that it requires the coupling of polarized monochromatic light to a metal surface using prisms, grating couplers, or integrated optical waveguides structures.

Schalkhammer et al. (Sensors and Actuators B 24-25 166 (1995)) used an optical thin-film resonance system consisting of a metal mirror, covered by a thin layer of an optically transparent pH-sensitive swelling polymer and a metal-island film. The system is characterized by a narrow reflection minimum, whose spectral position shifts with the interlayer thickness. By monitoring the slope of the characteristic (narrow-bandwidth) reflection minimum, 1% change of the absorption could be measured at a fixed wavelength for a change of 0.1% of the polymer thickness. A disadvantage of this method is that the interlayer thickness is dictated by the optical resonance condition of the metal-island/polymer/mirror system, leading to an interlayer thickness of several hundreds of nanometers for reflection minimum in the visible range. The sensor's response time can therefore not be reduced by decreasing the thickness of the interlayer.

McCurley (Biosensors and Bioelectronics 9 527 (1994)) use(s) fluorophores in a hydrogel. Protonation of the amine moiety in the hydrogel caused the gel to expand. An increase in the gel volume resulted in a decrease in the concentration of the dye in the gel since the amount of the dye in the gel remains constant, leading to decrease in fluorescence intensity. A slow response time ~10 min was observed, probably due to the need for the solvent to diffuse into the gel matrix.

Nevertheless, a need remains for gas sensing devices of low complexity, small size, and high sensitivity.

DEFINITIONS

Nanoparticle: a particle with dimensions in the range of 1-500 nm, preferably in the range of 2-200 nm, having any shape considered suitable by the person skilled in the art, such as for instance round, triangular or rectangular, and showing localized surface plasmon resonance upon illumination with light.

Quantum dot: a particle with dimensions in the range of 2-50 nm, preferably in the range of 2-10 nm, and showing photoluminescence upon illumination with light.

DISCLOSURE OF THE INVENTION

It is an aim of the present invention to provide a gas sensor which allows sensitive detection without the complexity, cost, and size of existing optical systems. Other aims of the present invention are to provide a method for manufacturing such a gas sensor and to provide a method for operating such a gas sensor.

These aims are achieved with the subject of the independent claims.

Existing gas sensors can operate at high sensitivity, but are often complex, large, and produced at a relatively high cost. To overcome such limitations, the present invention combines the use of specific layers with optical phenomena that occur on about the nanometer scale.

The gas sensor according to the present invention comprises a nanoparticle layer and a quantum dot layer, separated from each other by a gas absorption layer. The nanoparticle layer is provided for generating a surface plasmon resonance within a plasmon resonance frequency range upon illumination with light within the light frequency range; the quantum dot layer has an absorption spectrum overlapping with said plasmon resonance frequency range of said nanoparticle layer and shows photoluminescence in a photoluminescence emission frequency range upon absorption of energy within its absorption spectrum. This combination allows the detection of gases or small molecules by using nanoscale materials and optical phenomena that are occurring on the nanometer scale, thus enabling lower detection limits and faster response times.

Upon absorption of a gas by the gas absorption layer, the optical thickness of the gas absorption layer will change. This gas-induced swelling or shrinking of the gas absorption layer will change the distance between the nanoparticle layer and the quantum dot layer and as a result, will affect the photoluminescence emission intensity of the quantum dots. This information may then be used in the detection of gases and in obtaining specific information of these gases.

In fact, in the present invention, the concentration of the gas molecules is determined by the extent of swelling or shrinking of the gas absorption layer, which is positioned between the nanoparticle layer and the quantum dot layer. This permits use of the sensor as a solid state device in gaseous environments.

As the gas absorption layer can be fabricated with monolayer thickness control, fast response times and a low detection limit can be achieved.

The photoluminescence of the quantum dots is enhanced by the local electromagnetic field from the nanoparticles, which can lead to a higher sensitivity of the gas sensor.

In a preferred embodiment, the sensing mechanism is based on two competing mechanisms. The first mechanism involves the quenching of quantum dot photoluminescence by Förster resonance energy transfer from the quantum dots to the nanoparticles. It has been found that quenching of photoluminescence by nanoparticles or a rough metallic surface takes place at small distances, such as on the order of about a few nanometers. FRET (fluorescence energy transfer) is a mechanism where energy is transmitted without physical contact over short distances (from about 2 to about 10 nm) by a nonradiative, long-range dipole-dipole coupling mechanism between a donor chromophore in its excited state and an acceptor chromophore. Due to the dipole-dipole coupling mechanism, the FRET efficiency E depends on the distance r between the donor and the acceptor with an inverse 6th power law:

$$E=1/[1+(r/R_0)^6],$$

with $R_0$ being the Förster distance of this pair of donor and acceptor at which the FRET efficiency is 50%. The Förster distance depends on the overlap integral of the donor emission spectrum with the acceptor absorption spectrum and their mutual orientation. Gold nanoparticles are known to be effective quenchers of quantum dots photoluminescence by FRET.

The second mechanism involves enhancement of the quantum dot photoluminescence by the same nanoparticles of the nanoparticle layer. Due to their surface plasmon resonance, the nanoparticles can enhance the local electromagnetic field within a distance of about several tens of nanometers. Gold, silver, and copper nanoparticles are known to locally enhance the electromagnetic field by their localized surface plasmon resonance. This has been used for surface enhanced Raman spectroscopy. Surface plasmons are electron oscillations at optical frequencies which are localized to the interface between a medium with a positive dielectric constant and a medium with a negative dielectric constant, such as gold, silver, copper, and aluminium. Typically, gold, silver, and copper have surface plasmon resonances in the visible spectrum. In nanoparticles of these metals, plasmons can be directly excited by white light illumination. The exponentially decaying evanescent field resulting from the surface plasmon resonance is responsible for the local enhancement of the electromagnetic field around the metal nanoparticles. In the case of closely spaced pairs of metallic nanoparticles, the plasmons are able to couple with each other, leading to large enhancements of up to about two orders of magnitude in the electromagnetic field between the particles.

The competition between quantum dot photoluminescence quenching and photoluminescence enhancement results in a change of the photoluminescence emission intensity of the quantum dots with changing distance between the nanoparticle layer and the quantum dot layer.

As the thickness of the gas absorption layer can be very well controlled (on about the nanometer scale), either quenching or enhancement of photoluminescence can be observed, depending on the starting thickness of the gas absorption layer, since the photoluminescence is largest for an optimal distance.

The plasmon resonance frequency spectrum preferably at least partly overlaps with the photoluminescence emission frequency spectrum in order to allow FRET to take place.

Preferably, the photoluminescence emission wavelength generated by the quantum dot layer differs from the plasmon resonance wavelength, i.e. the excitation wavelength. In that way, detection can be done at a different wavelength than the wavelength used for the excitation, avoiding interference between the different signals and resulting in low background noise.

Usually, the photoluminescence emission wavelength generated by the quantum dot layer will be higher than the excitation wavelength, because the excited electron of the quantum dot layer will fall back to a lower energy level before recombining.

More preferably, the wavelength of the peak plasmon resonance, i.e. the wavelength at maximum intensity of the plasmon resonance spectrum, is lower than the wavelength of the peak photoluminescence of the quantum dots, i.e. the wavelength at maximum intensity of the photoluminescence quantum dot spectrum. In this way interference between the different signals can be avoided and result in low background noise.

In a preferred embodiment, a gas sensing device is provided which comprises a plurality of gas sensing devices according to the present invention.

In a preferred embodiment at least two of said plurality of gas sensing devices comprises gas absorption layers with different thicknesses before absorption of the gas. Upon absorption of a gas, the thickness of the gas absorption layers of the different gas sensing devices will change and result in an according change of the photoluminescence emission intensity. The combination of these signals allows optimizing the gas sensing measurement and minimizes the risk of false positives related to other processes that may cause quenching of photoluminescence intensity. The different gas absorption layers can be made of the same or a different material for absorption of respectively the same or a different gas. In case at least two of the gas absorption layers are made of a different material, the system allows detecting several gases with one and the same device at about the same time.

In another preferred embodiment, at least two of said plurality of gas sensing devices comprises gas absorption layers made of different materials for absorption of different gases. The gas absorption layers of said at least two gas sensing devices may have the same or a different thickness. Such a device allows detecting several gases with one and the same device at about the same time.

Alternatively, the gas sensing system may comprises a number of gas sensing devices which comprise gas absorption layers which are made of the same material for absorption of the same gas, but with a different thickness, and a number of gas sensing devices which comprise gas absorption layers which are made of a different material for absorption of different gases with the same or different thickness.

The present invention further relates to the use of this sensing mechanism using a solid state device for detection of small molecules and gases in a gaseous environment. This is not straightforward, as specific binding agents that respond to small molecules and industrial gases are not readily available for use outside of the liquid environment.

The present invention further relates to a method for manufacturing such a gas sensing device.

BRIEF DESCRIPTION OF THE DRAWINGS

The invention will be further elucidated by means of the following description and the appended drawings.

DESCRIPTION OF THE DRAWINGS

Figure 1:
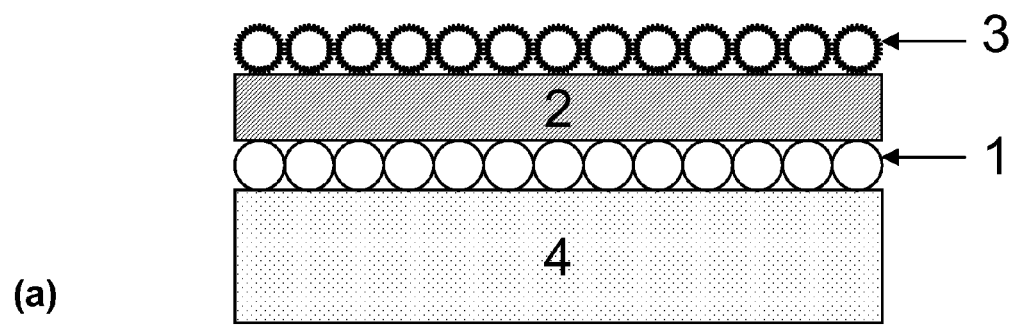
FIG. 1a shows the gas sensing device according to a first embodiment of the present invention.
FIG. 1b shows the gas sensing device according to a second embodiment of the present invention.
Figure 1:
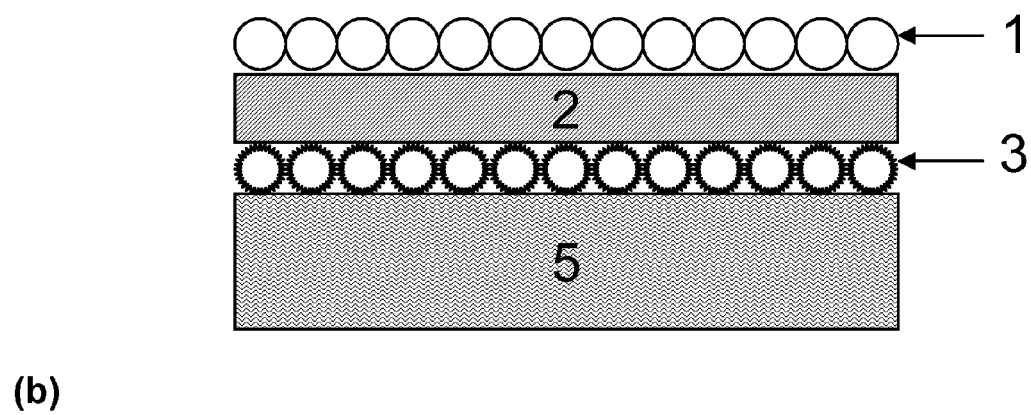

The present invention is described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third, and the like in the description and in the claims, are used for distinguishing between similar elements and not necessarily for describing a sequential or chronological order. The terms are interchangeable under appropriate circumstances and the embodiments of the invention can operate in other sequences than those described or illustrated herein.

Moreover, the terms top, bottom, over, under, and the like in the description and the claims are used for descriptive purposes and not necessarily for describing relative positions. The terms so used are interchangeable under appropriate circumstances and that the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

It should be understood that the illustrated embodiments are examples only and should not be taken as limiting the scope of the present invention. The claims should not be read as limited to the described order or elements unless stated to that effect. Therefore, all embodiments that come within the scope and spirit of the following claims and equivalents thereto are claimed as the invention.

FIG. 1a shows a first preferred embodiment of the gas sensing device according to the present invention. The gas sensing device comprises a nanoparticle layer 1, a gas absorption layer 2 and a quantum dot layer 3. The quantum dot layer 3 of the device shown in FIG. 1a forms a top layer of the device, but alternatively the quantum dot layer 3 can form a bottom layer of the device. The device shown in FIG. 1a further comprises a light emitting device 4 which emits light at about the wavelength corresponding to the plasmon resonance frequency of the nanoparticles of the nanoparticle layer 1. The light emitting device 4 may be any type of light emitting device considered suitable by the person skilled in the art, provided that the light being emitted by the light emitting device 4 is within a light frequency range which generates a plasmon resonance of the nanoparticles of the nanoparticle layer 1, such as for instance a LED which emits light at about the frequency corresponding to the plasmon resonance frequency. The light emitting device 4 is preferably in direct contact with the nanoparticle layer 1 as is shown in FIG. 1a. The light emitting device can also be placed at the side of the nanoparticle layer at a certain distance or at the side of the quantum dot layer, in direct contact with or at a certain distance from the quantum dot layer.

FIG. 1b shows a second preferred embodiment of the gas sensing device according to the present invention. Similar to the device shown in FIG. 1a, the gas sensing device comprises a nanoparticle layer 1, a gas absorption layer 2 and a quantum dot layer 3. The nanoparticle layer 1 forms a top layer of the device, but this need not be the case. The preferred embodiment shown in FIG. 1b further comprises a light detector 5 which is in direct contact with the quantum dot layer 3. The light detector 5 may be any type of light detector considered suitable by the person skilled in the art, provided that it is able to detect the photoluminescence emission frequencies of the quantum dot layer 3, such as for instance a photodiode. The light detector 5 is preferably in direct contact with the quantum dot layer 3 as is shown in FIG. 1b. The light detector can also be placed at the side of the quantum dot layer at a certain distance or at the side of the nanoparticle layer, in direct contact with or at a certain distance from the nanoparticle layer.

Alternatively, the gas sensing device according to the present invention may comprise a light emitting device 4 as well as a light detector 5, wherein the light emitting device 4 and the light detector 5 are placed at opposite sides of the nanoparticle/gas absorption layer/quantum dot layer stack. Preferably the light emitting device 4 is located at the side of the nanoparticle layer 1 and the light detector 5 is located at the side of the quantum dot layer 3. But it is also possible to place the light emitting device 4 at the side of the quantum dot layer 3 and the light detector 5 at the side of the nanoparticle layer 1. The light emitting device 4 and the light detector 5 can be in direct contact with the nanoparticle layer 1 and the quantum dot layer 3, or there can be a distance between the light emitting device 4 and/or the light detector 5 and the nanoparticle layer 1 and/or the quantum dot layer 3.

Figure 2:
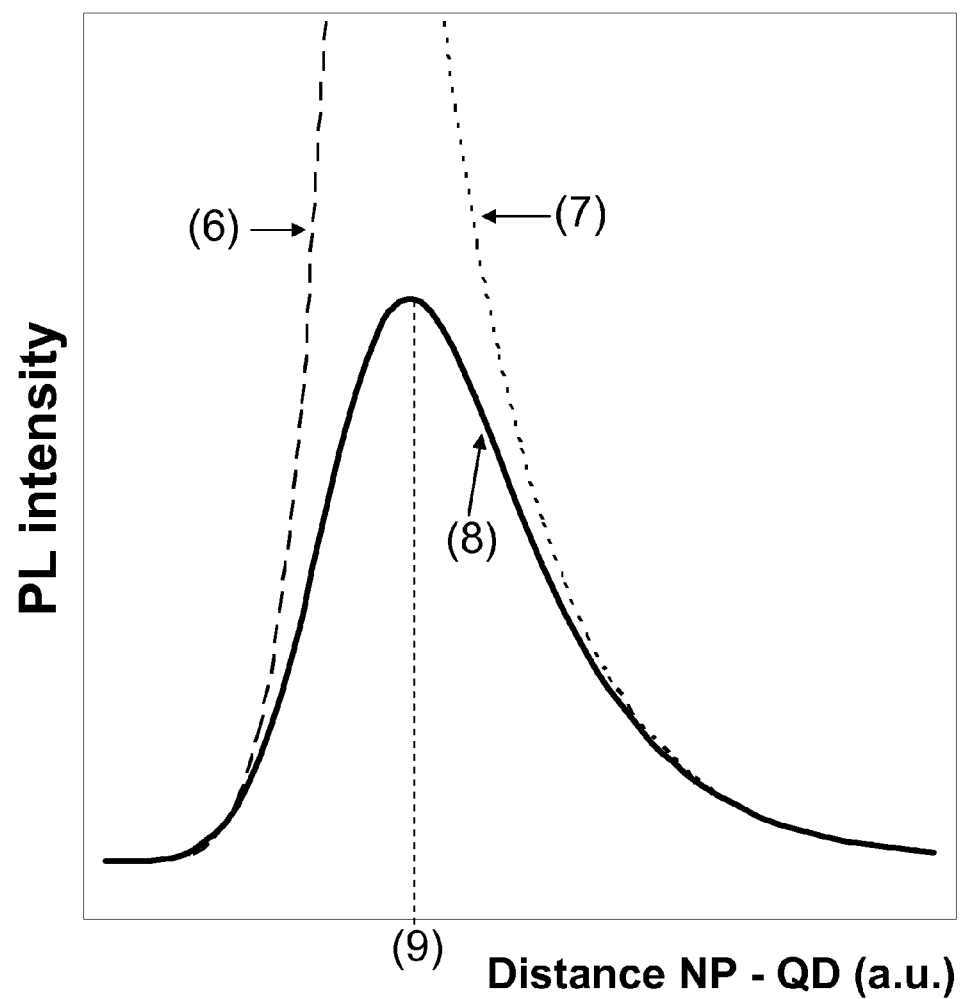
FIG. 2 shows the photoluminescence emission spectrum of the quantum dot layer, resulting from the competition between quantum dot photoluminescence quenching and quantum dot photoluminescence enhancement.

FIG. 2 shows the preferred sensing mechanism. The mechanism is based on distance-dependent competition between quantum dot photoluminescence quenching 6 by Förster resonance energy transfer from the quantum dots (QD) to the nanoparticles (NP), for example metallic gold nanoparticles, and quantum dot photoluminescence enhancement 7 due to the locally increased electromagnetic field near the nanoparticles, for example gold nanoparticles, by their surface plasmon resonance. The resulting quantum dot photoluminescence emission spectrum is represented by the full line 8.

Changes in the optimum distance 9 between the nanoparticles and the quantum dots, i.e. the distance between the nanoparticle layer 1 and the quantum dot layer 3 wherein the photoluminescence shows a maximum intensity, by swelling or contraction of the gas absorption layer 2, lead to a decrease in quantum dot photoluminescence as can be seen on the photoluminescence emission spectrum 8. Starting from the optimum distance 9 between the nanoparticles and the quantum dots, a decrease of this distance due to a contraction of the gas absorption layer will result in a decrease in quantum dot photoluminescence due to quantum dot photoluminescence quenching 6. An increase of this distance due to a swelling of the gas absorption layer will result in a decrease in quantum dot photoluminescence due to a reduced quantum dot photoluminescence enhancement 7. If the starting point is not the optimum distance then a decrease or increase in quantum dot photoluminescence can be achieved.

In some embodiments, the nanoparticle layer 1 may have a narrow plasmon resonance at wavelengths smaller than the photoluminescence wavelength of the quantum dots. In such cases, the density is preferably high enough to provide sufficient enhancement of the electromagnetic field in the vicinity of the nanoparticle layer.

Metallic layers, non-metallic layers, and combinations thereof are suitable for use as a nanoparticle layer. For example, non-metallic layers may be highly doped semiconductors, conductive metal oxides such as vanadium oxide or indium tin oxide. In embodiments using highly doped semiconductors, the plasmon resonance frequency may lie outside of the visible frequency range. For embodiments having a metallic nanoparticle layer, suitable materials may include gold (Au), silver (Ag), copper (Cu), aluminium (Al), nickel (Ni), and combinations thereof. Combinations of these metals may include alloys of two or more metals or layers of two or more metals. Gold (Au), silver (Ag), and copper (Cu) layers may, for example, have a plasmon resonance frequency within the visible spectrum.

In some embodiments of the invention, the nanoparticle layer comprises nanoparticles having an outer shell of any one of the above-mentioned metallic and non-metallic materials suitable for use in a nanoparticle layer. Preferably the shell is a conductive material and the core can be conducting or insulating (for example iron oxide surrounded by a Au shell). In some embodiments, gold (Au) is a suitable material for use in a nanoparticle layer because of its chemical stability. In yet other embodiments, silver (Ag) is a suitable material for a nanoparticle layer because of its strong plasmon resonance.

In some embodiments, the nanoparticle layer 1 comprises a uniform layer of nanoparticles of copper, gold, silver, or combinations thereof, where the nanoparticles have a diameter between about 2 nm and about 200 nm, or between about 5 nm and about 100 nm, or between about 10 nm and about 50 nm. For example, a nanoparticle layer 1 may comprise a uniform layer of nanoparticles, where the nanoparticles have a diameter between about 10 nm and about 20 nm. The shape of the nanoparticles need not be spherical; non-spherical nanoparticles may also be used. In fact, suitable nanoparticles may have any shape, for example, triangular, oval, square, and the like, as long as the feature results in narrow plasmon resonance at wavelengths smaller than the photoluminescence wavelength of the quantum dots. In some embodiments, the thickness of the nanoparticle layer corresponds to that of a single layer of nanoparticles.

Figure 11:
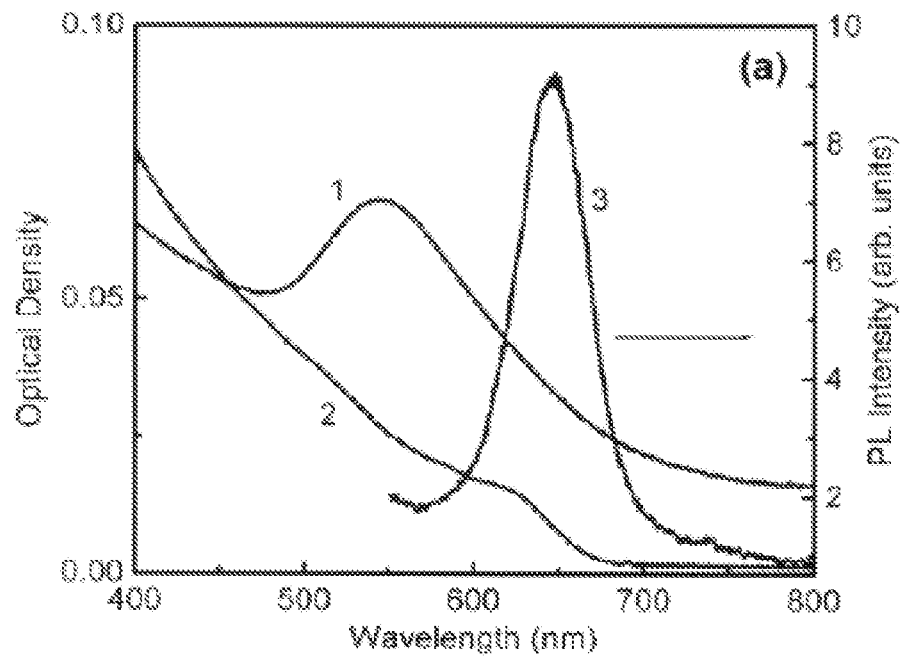
FIG. 11 shows the plasmon resonance spectrum, the quantum dot absorption spectrum and the quantum dot photoluminescence emission spectrum of a gas sensor according to a preferred embodiment of the invention.

FIG. 11 shows the plasmon resonance spectrum (1), the quantum dot absorption spectrum (2) and the quantum dot photoluminescence emission spectrum (3) of a gas sensor according to a preferred embodiment.

The quantum dot (QD) layer has an absorption spectrum that overlaps with the plasmon resonance frequency spectrum of the nanoparticle layer as shown in FIG. 11.

The frequency at which the photoluminescence spectrum shows a maximum intensity may be the same as or differ from the frequency at which the quantum dot layer shows a maximum intensity. As shown in FIG. 11, the optimum plasmon resonance frequency of the nanoparticles, i.e. the plasmon resonance frequency at maximum intensity, is preferably higher than the optimum photoluminescence frequency of the quantum dots, i.e. the quantum dot photoluminescence frequency at maximum intensity. In other words the wavelength of the peak plasmon resonance is preferably lower than the wavelength of the peak photoluminescence of the quantum dots. The fact that the peaks do not fall together allows reducing interference between the two signals and allows detecting the photoluminescence of the quantum dots better.

On the other hand the spectra (also outside the peak) of the plasmon absorption and the quantum dot photoluminescence preferably at least partly overlap in order to allow the FRET to take place, as is shown in FIG. 11.

The plasmon resonance wavelength of the nanoparticles may range between about 100 nm and about 3000 nm, or between about 800 nm and about 3000 nm, or between about 300 nm and about 800 nm, or between about 400 nm and about 700 nm. For example, the plasmon resonance of the nanoparticles may range between about 500 nm and about 600 nm.

The gas absorption layer 2 preferably comprises a material that allows for the selective absorption of the gas that one wants to detect. The gas absorption layer 2 typically swells upon absorbing the gas, thus allowing for sensitive detection of the gas.

A gas absorption layer 2 may comprise materials suitable for absorbing gases, such as polymers. Suitable gas-absorbing polymers include, but are not limited to, poly($\gamma$-aminopropylethoxy/propyl-ethoxysiloxane), poly($\gamma$-aminopropylethoxy/octa-decylethoxysiloxane), poly(ethylene-vinyl acetate), polydimethylsiloxane, polyether-urethane, cynaopropylmethyl-dimethylsiloxane, poly(vinyl acetate), poly(iso-butyrene), polycarconate urethane, and conductive polymers. Other suitable gas-absorbing materials include, but are not limited to, hydrogels, layers consisting of macromolecules such as dendrimers, and polyelectrolyte multilayers (PEM) such as poly(styrene sulfonate) (PSS)/poly(diallyldimethylammonium chloride) (PDADMAC) and the like.

In one embodiment, a gas absorption layer 2 suitable for the detection of $CO_2$ gas, comprises at least one of poly($\gamma$-aminopropylethoxy/propyl-ethoxysiloxane) and poly($\gamma$-aminopropylethoxy/octadecylethoxysiloxane). In other embodiments, a gas absorption layer 2 suitable for the detection of toluene and/or benzene comprises poly(ethylene-vinyl acetate). In other embodiments, a gas absorption layer suitable for the detection of at least one of n-octane, toluene, and 1-butanol comprises at least one of polydimethylsiloxane, polyetherurethane, and poly-(cynaopropylmethyl-dimethylsiloxane). In another embodiment, a gas absorption layer suitable for the detection of at least one of toluene, tetrachloroethylene, and 1-propanol comprises a dendrimer.

The thickness of the gas absorption layer 2 may be any thickness considered suitable by the person skilled in the art.

The thickness of the gas absorption layer 2 is preferably chosen such that the photoluminescence is at least near (if not at) the maximum 9 of the curve represented in FIG. 2. For example, the thickness can range between about 50% and about 200%, or between about 70% and about 150%, or between about 80% and about 120%, or between about 90% and about 110%, based on the thickness 9 corresponding to the maximum photoluminescence.

The thickness 9 corresponding to the maximum photoluminescence depends on the materials being used. For Au nanoparticles, for example, the maximum photo-luminescence occurs at about 15 nm. In some embodiments where the nanoparticle layer comprises gold nanoparticles, the thickness of the gas absorption layer can be between about 2 nm and about 100 nm, or between about 5 nm and about 50 nm, or between about 5 nm and about 30 nm, or between about 5 nm and about 25 nm, or between about 10 nm and about 20 nm.

According to a preferred embodiment, the thickness of the gas absorption layer 2 corresponds to the optimal distance 9 corresponding to the maximum photoluminescence intensity shown in FIG. 2. Indeed, upon absorption of the gas, the thickness of the gas absorption layer 2 will increase or decrease, resulting in a maximum decrease of the photoluminescence emission intensity of the quantum dots.

According to a preferred embodiment, the thickness of the gas absorption layer 2 is just beneath/above the optimal distance 9 corresponding to the maximum photoluminescence frequency shown in FIG. 2. Such a device reduces the risks of false positives. Indeed, upon absorption of the gas, the thickness of the gas absorption layer will increase/decrease, resulting first in a small increase/decrease of the photoluminescence emission intensity, followed by a large decrease/increase of the photoluminescence emission intensity.

The gas absorption layer 2 typically swells upon absorbing a gas. In some embodiments, the degree of swelling can range between about 40% and about 300%, or between about 50% and about 200%, or between about 70% and about 150%, based on the initial layer thickness for sensitive quantification of the amount of gas in the intended range of gas concentrations.

In some embodiments, the gas absorption layer 2 is a thin polyelectrolyte multilayer (PEM), for example, poly(styrene sulfonate) (PSS)/poly(diallyldimethylammonium chloride) (PDADMAC). In embodiments where the gas absorption layer comprises a PSS/PDADMAC multilayer, the PSS can act as a polyanionic layer and the PDADMAC can act as a polycationic layer. Hence, in such embodiments, layer deposition can be self-terminated by the electrostatic nature of the deposition method, thus allowing for a layer-by-layer deposition.

Gas-induced swelling of the gas absorption layer 2 increases the distance between the nanoparticles (NP) (for example, Au) and the quantum dots (QDs). This change in distance affects the photoluminescence (PL) intensity of the QDs. In some embodiments where the nanoparticle layer comprises gold nanoparticles, the thickness of the absorption layer can range between about 0 and about 30 nm. For some embodiments using gold nanoparticles, maximum PL efficiency is expected for a thickness of about 15 nm. A change in thickness of about 50% (either contraction or expansion) may reduce the photoluminescence to about its base level.

According to a preferred embodiment, a gas sensing system is provided which comprises a plurality of gas sensing devices according to the invention. In one preferred embodiment, at least two of said plurality of gas sensing devices comprise gas absorption layers with different thicknesses before absorption of the gas, the gas absorption layers being made of the same or a different material provided for respectively absorbing the same or a different gas. The combined responses of the gas sensing devices may be used for the detection of one or more gases and reduces the risk of false positives. Such a device is in particular preferred in case the optimal distance between the quantum dot layer and the nanoparticle layer is not known or difficult to manufacture. Usually, the plurality of gas sensing devices will comprise a number of different gas absorption layers with different thicknesses and comprising a material which is selective for the same gas. In another preferred embodiment, the gas sensing system comprises a plurality of gas sensing devices, at least two of said plurality of gas sensing devices comprising gas absorption layers made of different materials for the selective absorption of different gases. The different layers may have the same thickness or a different thickness. Preferably, the thickness of the different layers will be equal to or close to the optimal distance 9 for that specific material. The combined responses of the sensors in the array may be used for the detection of different gases.

In other embodiments, non-selective gas absorption layers are used. In such embodiments, a gas absorption device may additionally comprise an array of sensors. When a sensor array is used in combination with a non-selective gas absorption layer, the combined responses of the sensors in the array may be used to identify the gas.

The quantum dot layer 3 preferably comprises a material selected from the group consisting of semiconductor nanocrystals, such as CdSe/ZnS core/shell QDs; combinations of II/VI or III/V compounds, such as CdTe/ZnS; semiconductor nanocrystals comprising II/VI compounds such as CdSe, CdTe, CdS, ZnS, ZnSe, PbTe, PbSe, PbS, CdSe/ZnS, CdTe/ZnS, and the like; various III/V compounds, such as InAs, InP, InN, GaAs, GaN and combinations thereof; core/shell quantum dots comprising at least one of the previously listed quantum dot materials and combinations thereof; and metal oxides, such as ZnO, or any combinations thereof.

Illumination can occur by any suitable means 4 known to those of skill in the art. For example, illumination can occur through the use of a light emitting diode, a laser, a white light source, and the like. In some embodiments, illumination can be done in the form of white light or another broad-band light source, and a cut-off filter can be used between the nanoparticles and the quantum dots to avoid direct excitation of the quantum dots. In some embodiments, illumination is done at or near the plasmon resonance frequency of the nanoparticle layer using an LED as the excitation source.

The transducer layers may, for example, be fabricated directly on a light emitting diode (LED) 4 which can emit light of a wavelength that approximately corresponds to the plasmon resonance frequency of the nanoparticle layer (see FIG. 1(a)). For some embodiments where the nanoparticle layer 1 comprises gold nanoparticles, the LED can emit light at a wavelength of about 550 nm. In some embodiments employing a LED as a substrate, the LED can comprise inorganic materials including, but not limited to, combinations of the following semiconductor materials and their alloys: AlAs, GaAs, GaP, InAs, GaN, InN, AlN; or can comprise organic materials including, but not limited to, light emitting organic molecules or polymers.

Detection of an emission can be carried out using devices 5 well known to those of skill in the art. Such a device includes, but is not limited to, photodiodes, CCD cameras, photovoltaic cells, and the like.

In some embodiments, a photodiode is used to measure the quantum dot photoluminescence at a wavelength larger than the plasmon resonance wavelength of the nanoparticles. In embodiments where the nanoparticle layer comprises gold nanoparticles having a plasmon resonance frequency of about 550 nm, the quantum dot photoluminescence may be measured for example at a wavelength of about 620 nm. In some embodiments, the transducer is fabricated directly on a photodiode 5 (see FIG. 1(b)), such that the photodiode is used as the substrate. In embodiments where a photodiode is used as a substrate, the photodiode can comprise inorganic materials including, but not limited to, AlAs, GaAs, GaP, InAs, GaN, InN, AlN, and alloys or combinations thereof, as well as other inorganic photosensitive metal oxides, such as ZnO. In some embodiments, the photodiode can comprise organic materials including, but not limited to, light sensitive organic molecules or polymers, and combination of organic materials with inorganic materials.

In some embodiments, a fully integrated gas sensor can comprise a transducer, a light source 4, and a detector 5. In FIG. 1(a), for example, the transducer is made on an LED. In some such embodiments, a fully integrated sensor can result by fabricating a photodetector, such as a photodiode, on top of the transducer. In FIG. 1(b), for example, the transducer is made on a photodiode. In some such embodiments, a fully integrated sensor can result by fabricating an LED on top of the transducer.

In cases where the gas needs to be measured in a recipient, a deposition chamber, or other closed environment, the sensor and, if present, the LED on which the sensor is deposited, can be mounted on a feedthrough having connections to transport the signal to the outside world. Alternatively, LED and photodiode may be positioned outside the recipient in order to avoid having electrical connections running from inside the closed environment to the outside world.

The signal of the photodiode can be sent to a computer interface, and suitable software can be used to calculate the concentration of the gas based on the nature of the gas, as well as the composition and thickness of the gas absorption layer.

In some embodiments, an organic photodiode/photovoltage cell for detection can be used to reduce the used power. This is advantageous since the sensor can be used with a limited power supply. Using organic light emitting diodes and organic photovoltaic devices, the light source and detector can be fine-tuned with respect to their spectral responses.

In embodiments where more than one different gas needs to be detected, several gas sensors can be arranged in an array, where each of these gas sensors has a gas sensing layer with suitable thickness and/or composition adapted for the detection of a particular gas. Alternatively, non-selective gas absorption layers can be used for the detection of different gases. In such embodiments, the combined responses of the sensors in the array may be used to identify the gas. Each of these sensors can be placed between an LED array and an (in)organic photodiode/photovoltage array. The sensors in the array can be used together to measure in parallel different gases.

The device may be extended with electrical readout by incorporation of (transparent) electrodes on (parts of) the sensing array. For example, by placing electrodes on both the substrate and on top of the transducer layers, capacitive readout becomes possible. The capacitance of the device will change upon swelling or contraction of the absorption layer, which acts as the dielectric in this case.

Alternatively, tunnelling currents and/or ionic conductivity between the nanoparticles, or through the absorption layer 2, may be used for electronic readout of the sensor by modification of the sensor by incorporation of electrodes. For example, the absorption layer 2 may be made thin enough for tunnelling to occur between contacts fabricated above and below the absorption layer. Since the tunnelling current depends exponentially on the distance between the contacts, it can be sensitive to gas absorption. In case of a thicker absorption layer, ionic conductivity may be measured between the contacts. The resistivity of the absorption layer 2 may change by gas absorption. Also, a tunnelling current between the Au nanoparticles themselves may be measured if the interparticle distance is small enough.

In some embodiments, fabrication of the gas sensing device can start with the fabrication of a monolayer of nanoparticles on a substrate.

In some embodiments, the substrate is a transparent substrate, such as glass or quartz. In other embodiments, the substrate is a LED.

The nanoparticle layer 1 can be deposited by any suitable technique known to those of skill in the art. Suitable techniques include, but are not limited to, spin coating, drop casting, Langmuir-Blodgett techniques, and the like. In some embodiments, the nanoparticles are deposited as a thin metal film, which breaks up into nanoparticles after annealing. In other embodiments, deposition of charged nanoparticles from solution is used. In embodiments where nanoparticles are deposited from solution, the substrate may be covered with a layer of polycations or polyanions for the electrostatic binding of nanoparticles.

Films of nanoparticles can also be fabricated using lithographical patterning processes, such as electron-beam lithography or other lithographical patterning techniques. Nanoparticles (e.g., gold or other materials) may also be fabricated using nanosphere lithography, where the substrate is covered with a layer of closely packed spherical particles on top of which the nanoparticle layer of gold or other material is deposited. After removal of the spherical particles, the nanoparticle material (e.g., gold or other material) that had once filled the gaps between the spherical particles stays behind, forming a nanoparticle layer. In other embodiments, nanoparticles (e.g., gold) may be patterned using a deposition technique where the nanoparticle material, such as gold, is encapsulated in an organic material in the form of micelles, forming a layer on the substrate. After removal of the organic material (e.g., by annealing), the nanoparticle material, such as gold, remains on the substrate. Other techniques for creating nanoparticles may be used; the above description is offered for illustrative purposes and is not intended to be exhaustive.

After deposition of the nanoparticle layer 1, the gas absorption layer 2 is deposited. The gas absorption layer 2 may be deposited by any suitable technique known to those of skill in the art. Suitable techniques include, but are not limited to, spin coating, drop casting, Langmuir-Blodgett film deposition, evaporation, atomic layer deposition, and the like. In some embodiments, good control of the layer thickness can be achieved by depositing the layer as a polyelectrolyte multilayer having alternating polycationic and polyanionic layers. Polyelectrolyte multilayers can be particularly suitable when the gas absorption layer is to be deposited onto a non-flat surface. Preferably, though not exclusively, the absorption layer 2 does not substantially absorb light in the spectral range corresponding to that of either the plasmon resonance of the metallic nanoparticles or the quantum dot absorption spectrum.

The quantum dot layer 3 is fabricated by deposition of QDs on top of the gas absorption layer 2. The quantum dot layer 3 may be deposited by any suitable technique known to those of skill in the art. Suitable techniques include, but are not limited to, spin coating, drop casting, Langmuir-Blodgett film deposition, and the like. In some embodiments, the quantum dot layer 3 comprises a monolayer of quantum dots which have equal distance to the nanoparticle layer 1. In some embodiments, the quantum dot coverage is homogeneous. Additionally, in some embodiments, other fluorophores, such as molecular dyes, may be used.

An external photodiode 5 can be used to measure the quantum dot photoluminescence. In some embodiments, a photodiode is fabricated on the quantum dot layer 3. In a further embodiment, a photodiode is included in the quantum dot layer 3, for example the quantum dot layer 3 may comprise a light-sensitive organic layer.

In alternative embodiments, the fabrication of a gas sensor can start with the deposition of quantum dots on a substrate. In some embodiments, the substrate is a transparent substrate, such as glass or quartz. In other embodiments, the substrate is a photodiode. On the quantum dot layer, a gas absorption layer is deposited. Suitable techniques for the deposition of a gas absorption layer are described above. The nanoparticle layer is fabricated on the gas absorption layer. Suitable techniques for the deposition of a nanoparticle layer are described above. In some embodiments, an external LED is used to excite the plasmon resonance of the gold nanoparticles. In some embodiments, a LED is fabricated on the nanoparticle layer. In a further embodiment, a LED is included in the quantum dot layer, for example the quantum dot layer may comprise a light-emitting organic layer.

Methods of using the gas sensing device include illuminating the nanoparticle layer 1 with light at a wavelength corresponding to the plasmon resonance of the nanoparticle layer. In some embodiments, illumination occurs through the use of a LED. In some embodiments, illumination occurs through the use of a white or other broad-band light source, and a cut-off filter is used in order to prevent direct excitation of the QDs. In some embodiments, a cut-off filter is placed between the light source (e.g., LED, broad-band source, etc.) and the nanoparticles.

If the thickness of the gas absorption layer 2 is larger than the optimal thickness 9 corresponding to the highest quantum dot photoluminescence, the quantum dot photoluminescence will be suboptimal due to the exponentially decaying strength of the local electromagnetic field extending from the gold nanoparticles. If the thickness of the absorption layer is lower than that corresponding to the highest quantum dot luminescence, the quantum dot layer luminescence will be suboptimal due to quenching by FRET due to its proximity to the gold nanoparticle layer.

The resulting quantum dot luminescence is detected by a detector, for example a photodiode, and recorded. Other suitable photodetectors are described above. In some embodiments, the signal of the photodiode is sent to a computer comprising software for detection and analysis of the detector signal.

The device is then exposed to vapours or gases which are to be detected. In case of swelling of the absorption layer by exposure to the vapours or gases, the quantum dot luminescence is decreased, leading to a decrease in the recorded signal, if the thickness of the gas absorption layer before gas exposure is larger than that corresponding to the highest photoluminescence. If the thickness of the absorption layer before exposure to gases or vapours was less than that corresponding to the highest quantum dot photoluminescence, the quantum dot photoluminescence is increased, leading to an increase in the recorded signal. Inversely, if the absorption layer contracts after exposure to gases or vapours, the quantum dot luminescence is increased, leading to an increase in the recorded signal, in case the thickness of the gas absorption layer before gas exposure is larger than that corresponding to the highest photoluminescence. If the thickness of the absorption layer before exposure to gases or vapours was less than that corresponding to the highest quantum dot photoluminescence, the quantum dot photoluminescence is decreased, leading to a decrease in the recorded signal.

For analysis, it may be determined whether the thickness of the gas absorption layer prior to gas absorption is larger or smaller than that corresponding to the highest quantum dot luminescence. This may be determined prior to the measurement. Therefore, calibration of the sensing device can be done. Or a multitude of sensing devices may be used, each with a different thickness in a range around the optimal thickness corresponding to the highest quantum dot photoluminescence. By tracking the response of these devices, expansion or contraction of the absorption layer may be determined. This can be done with a computer comprising software for analysis of the detector signals.

Example 1

Formation of the Absorption Layer

Silicon substrates were cleaned using piranha solution ($H_2SO_4/H_2O_2$ 3:1 v/v) and thoroughly rinsed with water. After rinsing, polyelectrolyte multilayers with different thickness were deposited and their thickness was determined by ellipsometry measurements.

Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared with concentrations of 0.01 M in water (DI) and 0.02 M in 0.1 M NaCl. Polymer concentrations refer to the number of monomers (which equals the number of charges, as both polymers are strong electrolytes with one charge per monomer).

As the substrates were negatively charged, PDADMAC was always adsorbed first. Substrates were immersed in one polymer solution, rinsed with water, blown dry with hot air and immersed in the other, oppositely charged, polymer solution. This was continued until the desired number of layers, e.g., up to 15 layers, was deposited.

Figure 3:
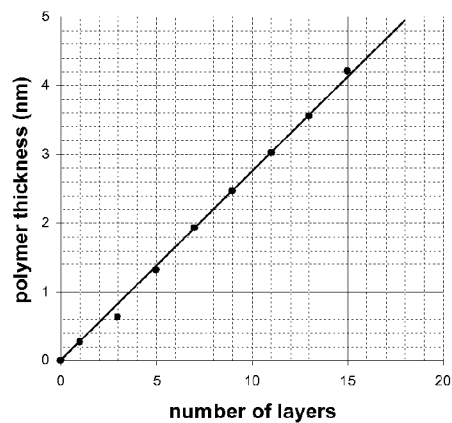
FIG. 3 shows the overall polyelectrolyte multilayer thickness as a function of the number of polymer layers.
Figure 3:
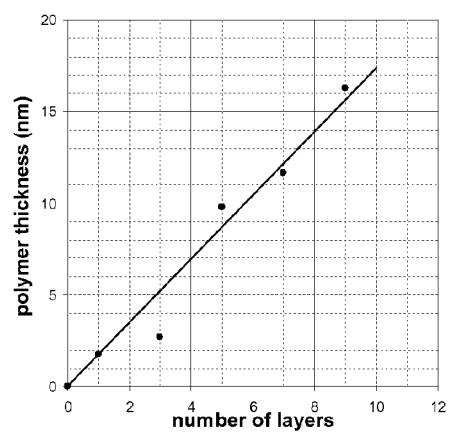

The first experiments were done with 0.01 M polymer solutions in water and immersion times of 30 minutes per layer. As shown in FIG. 3(a), this leads to adsorption of very thin polymer layers. The thickness of one polycation layer corresponds to 0.28 nm. When using a higher polymer concentration (0.02 M) and adding some salt (0.1 M NaCl), much thicker polymer layers are obtained. In this case, the thickness of one polycation layer corresponds to 1.73 nm per layer (see FIG. 3(b)).

Example 2

Dynamics of Absorption Layer Formation

Silicon substrates were cleaned using piranha solution ($H_2SO_4/H_2O_2$ 3:1 v/v) and rinsed with water. After rinsing, five polyelectrolyte layers were deposited with immersion times (per layer) varying between 15 seconds and 10 minutes and their resulting thickness was determined by ellipsometry measurement in order to investigate how long it takes before the maximum layer thickness is reached.

Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared with concentrations of 0.01 M in DI water and 0.02 M in 0.1 M NaCl.

Figure 4:
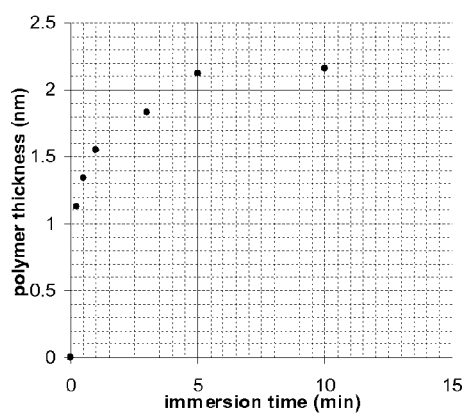
FIG. 4 shows the thickness of a five-layer polyelectrolyte multilayer as a function of the immersion time.
Figure 4:
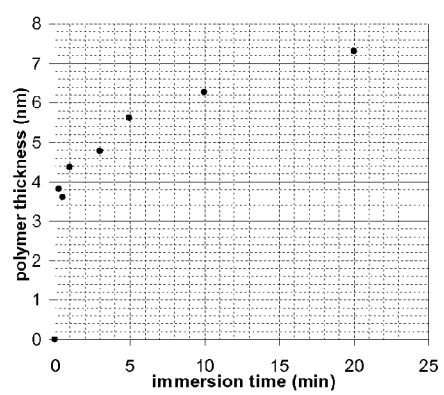

FIG. 4(a) shows that thickness of a 5 polyelectrolyte layer saturates in approximately five minutes when polymer solutions were prepared with concentrations of 0.01 M in DI water.

When using polymer solution prepared with concentrations of 0.02 M in 0.1 NaCl, it takes more time to reach the plateau adsorption (FIG. 4(b)). Initial adsorption is very fast (almost 4 nm with an immersion time of 15 seconds). After that the slope decreases, but even after 20 minutes a true plateau is not observed. This indicates that in order to maximize the layer thickness, immersion times longer than 20 minutes may be needed.

Example 3

Formation of the Au Nanoparticle Layer Studied by SEM

Silicon substrates were cleaned using piranha solution ($H_2SO_4/H_2O_2$ 3:1 v/v) and thoroughly rinsed with water. After rinsing, five polyelectrolyte layers were deposited with immersion times of 15 seconds for each layer.

Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared with concentrations of 0.01 M in water (DI) and 0.02 M in 0.1 M NaCl.

Au nanoparticles (Au NP) were then deposited on the substrates. A commercially available Au nanoparticle solution (radius 5 nm, $7\times10^{12}$ particles/ml) was used. The solution was diluted 5 times before use.

The multilayers were deposited on the substrates before deposition of Au NP, in order to ensure good adsorption of the (negatively charged) Au NP. The 5-layer PEM was terminated by positively charged PDADMAC. The substrates were immersed in the Au NP solution for 2 hours. SEM images clearly show a higher density of Au NP on a PEM layer prepared from polymer solutions with concentrations of 0.02 M in 0.1 M NaCl compared to that of Au NP on a PEM layer from polymer solutions with concentrations of 0.01 M in water.

This indicates that using a PEM layer deposited from polymer solutions with concentrations of 0.02 M in 0.1 M NaCl may lead to a stronger plasmon resonance absorption compared to using a PEM layer deposited from polymer solutions with concentrations of 0.01 M in water.

Example 4

Formation of the Au Nanoparticle Layer Studied with UV/VIS

Quartz substrates were cleaned using piranha solution ($H_2SO_4/H_2O_2$ 3:1 v/v) and thoroughly rinsed with water. After rinsing, five polyelectrolyte layers were deposited with immersion times (per layer) of 5 minutes.

Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Two types of polymer solutions were prepared, in the first type the concentration of the polymers was 0.01 M in water (DI), in the second type the polymer concentrations were 0.02 M in 0.1 M NaCl.

Au nanoparticles (Au NP) were then deposited on the substrates. A commercially available Au nanoparticle solution (radius 5 nm, $7\times10^{12}$ particles/ml) was used. The solution was diluted 5 times before use. Two gold NP solution were prepared. To the second solution 9 mM of NaCl was added.

Multilayers from the two types of polymer solutions were deposited on the substrates before deposition of Au NP, in order to ensure good adsorption of the (negatively charged) Au NP. The 5-layer PEM was terminated by positively charged PDADMAC. The substrates were immersed in the Au NP solutions for 2 hours.

UV/Vis spectra of Au NP deposited from the Au NP solution without added NaCl on the substrates prepared using the first type of polymer solutions, i.e. the solutions with polymer concentrations of 0.01 M in water show the characteristic surface plasmon peak around 520 nm, but the absorption is very weak (FIG. 5, solid curve), indicating that the number of adsorbed particles is small.

Figure 5:
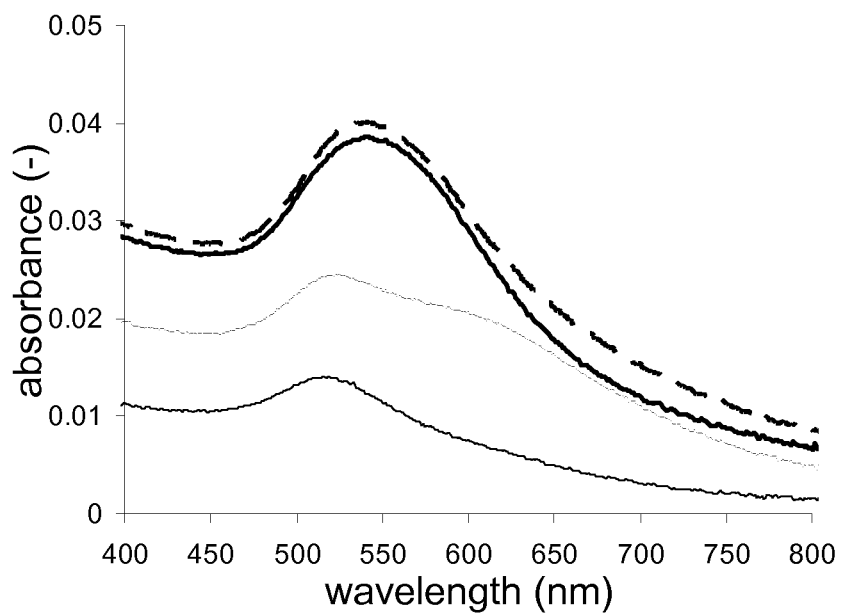
FIG. 5 shows the UV-Vis spectrum of a deposited gold nanoparticle.

When the Au NP are adsorbed from the 9 mM NaCl solution instead of pure water there is a significant increase in the UV/VIS absorption (FIG. 5, dotted curve). Beside the increase in absorbance, a shoulder appears in the spectrum around 600 nm.

When the substrates were prepared using the second type of polymer solutions, i.e. the solutions with polymer concentrations of 0.02 M in 0.1 M NaCl, the addition of NaCl to the Au NP solution has much less effect (FIG. 5, dashed curves). This can be explained by the fact that the charges in the PEM layers deposited from these solutions compensate for the Au NP electrostatic repulsion even without the addition of NaCl.

Example 5

Fabrication of Water Soluble QDs and Photoluminescence

For the fabrication of water soluble quantum dots (QDs) commercially available suspensions of CdSe/ZnS QD (radius 2.6 nm, $6\times10^{15}$ particles/ml in toluene) were used. The QDs were made water soluble by chemically by attaching negatively charged molecules (mercaptoacetic acid) to the QDs.

A solution in chloroform of mercaptoacetic acid (MAA, 10 g/l=0.11 M) and di-isopropylethylamine (DIPEA, 20 g/l=0.15 M, 1.5 eq.) was prepared. DIPEA is an organic base which removes the proton from MAA. 9 parts by volume of the MAA/DIPEA solution were added to 1 part of the QD solution (as received). The excess of MAA over QD is a factor $10^5$. The reaction mixture is sonicated for 1 minute and stirred at 62° C. (reflux) for 20 hours while $N_2$ is gently blown over the solution. During the reaction, the QD become insoluble in chloroform and precipitate.

The reaction mixture was centrifuged (2500 rpm, 10 minutes), washed with chloroform and centrifuged again. This procedure was repeated two more times before MAA-QD were dried in a $N_2$ stream for 30 minutes. Then, they were dissolved in 10 times diluted phosphate buffer (pH 7.2) to a concentration of 0.5 g/l, sonicated and centrifuged one more time. The supernatant had a yellow/orange color and was diluted five times with PDADMAC solution (0.01 M, no added salt). Thus, a polymer-QD complex was formed.

Figure 6:
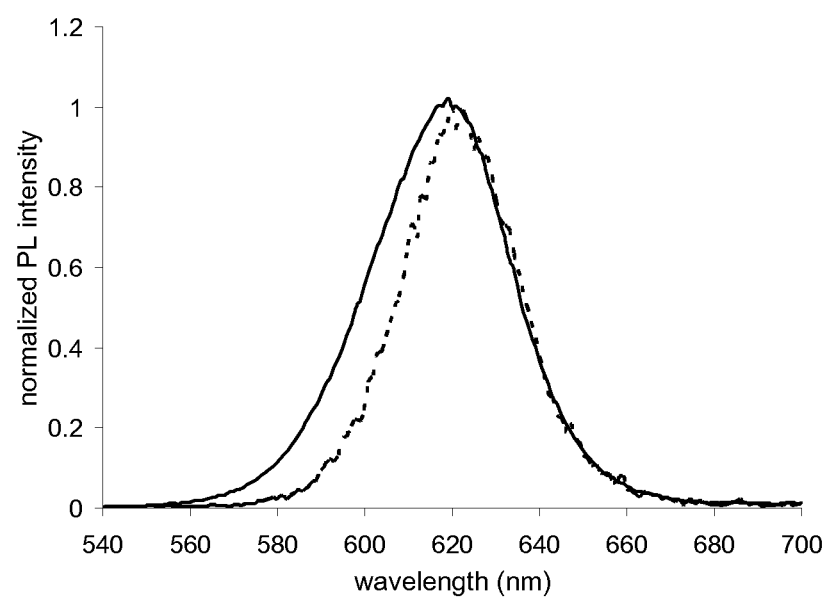
FIG. 6 shows the emission spectra of quantum dots in different solvents.

Photoluminescence (PL) emission spectra were measured of both the QD/toluene and QD/PDADMAC solutions. When excited at 439 nm, the both the QD/toluene (full line in FIG. 6) and the QD/PDADMAC (dotted line in FIG. 6) solutions showed a PL emission peak at 620 nm (FIG. 6).

Example 6

Deposition and Photoluminescence of the QDs Layer

Quartz substrates were cleaned using piranha solution ($H_2SO_4/H_2O_2$ 3:1 v/v) and thoroughly rinsed with water. After rinsing, four polyelectrolyte layers were deposited with immersion times (per layer) of 5 minutes.

Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared, with a concentration of 0.02 M in 0.1 M NaCl.

The substrates were then immersed in the MAA-QD/PDADMAC solution described in Example 5 for 30 minutes. The complex of negatively charged MAA-QD and positively charged PDADMAC in the MAA-QD/PDADMAC solution has a net positive charge, since the QD concentration (~$10^{-8}$-$10^{-7}$ M) is orders of magnitude lower than the polymer concentration ($10^{-2}$ M). Therefore, a 4-layer PEM was used since it was terminated by a negatively charged PSS layer.

Figure 7:
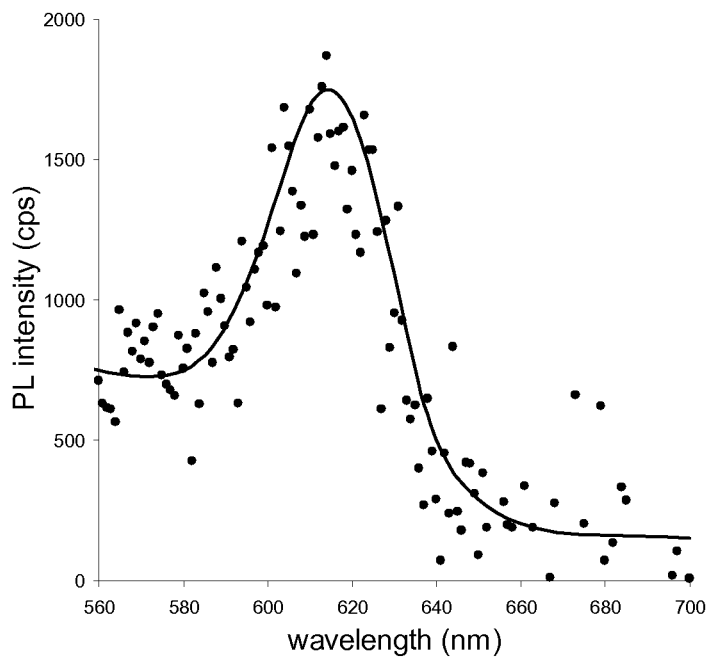
FIG. 7 shows the differential emission spectrum of quartz substrates with and without quantum dots.

The photoluminescence PL emission spectrum of the substrates with and without adsorbed QDs was recorded using an excitation wavelength of 439 nm. The differential spectrum, showing only the contribution from the QDs, is shown in FIG. 7. A clear emission peak around 620 nm was observed indicating that QD deposition was successful and that the emission wavelength did not significantly change upon transfer from solution to the solid substrate.

Example 7

Fabrication and Photoluminescence of the Entire Stack

Quartz substrates were cleaned using piranha solution ($H_2SO_4/H_2O_2$ 3:1 v/v) and rinsed with water. After rinsing, a 5-layer PEM was deposited using a deposition time of 5 minutes per layer. Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared, with a polymer concentration of 0.02 M in 0.1 M NaCl.

Then, the substrate was immersed in the Au NP solution for 75 minutes to ensure good coverage. A commercially available Au NP solution (radius 5 nm, $7\times10^{12}$ particles/ml) was used. The solution was diluted 5 times before use.

The next step was deposition of a 36-layer (10 nm) PEM using a deposition time of 5 minutes per layer from solutions with a polymer concentration of 0.01 M in water.

Finally, the substrates were immersed in the above described MAA-QD/PDADMAC solution for 30 minutes. Substrates were blown dry after every single deposition step.

Figure 8:
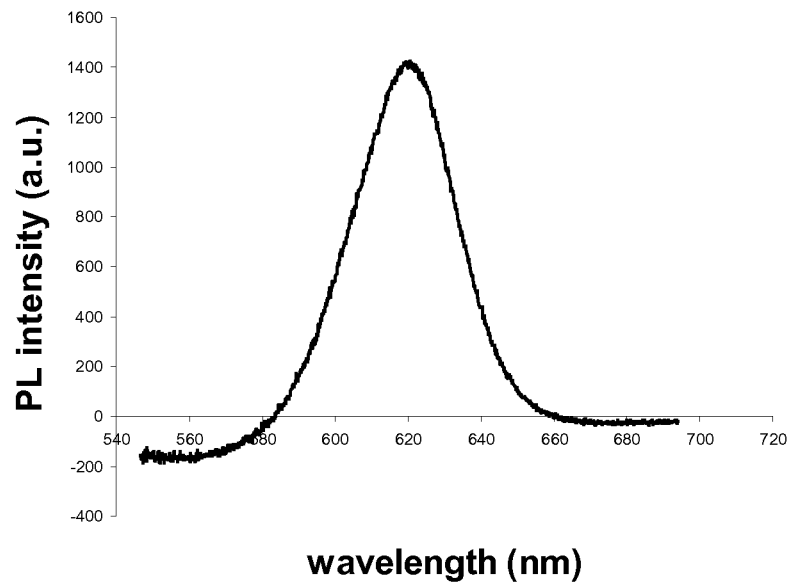
FIG. 8 shows the emission spectrum of the complete transducer stack after deposition on quartz substrates.

PL emission spectra (excitation wavelength 457 nm) of the substrates were measured. PL spectra were recorded using a confocal Raman microscopy set-up. The sample showed a clear QD emission peak at 620 nm as shown in FIG. 8.

Example 8

Fabrication and Photoluminescence of the Entire Stack

Quartz substrates were cleaned using piranha solution ($H_2SO_4/H_2O_2$ 3:1 v/v) and rinsed with water. After rinsing, a 5-layer PEM was deposited using a deposition time of 5 minutes per layer. Poly(styrene sulfonate) (PSS, Mw=$2\times10^5$ g/mol) was used as the polyanion and poly(diallyldimethylammonium chloride) (PDADMAC, Mw=$1-2\times10^5$ g/mol) as the polycation. Polymer solutions were prepared, with a polymer concentration of 0.02 M in 0.1 M NaCl.

Then, the substrate was immersed in the Au NP solution for 75 minutes to ensure good coverage. A commercially available Au NP solution (radius 5 nm, $7\times10^{12}$ particles/ml) was used. The solution was diluted 5 times before use.

The next step was deposition of a 36-layer (10 nm) PEM using a deposition time of 5 minutes per layer from solutions with a polymer concentration of 0.01 M in water.

Finally, the substrate was immersed in the above described MAA-QD/PDADMAC solution for 30 minutes. The substrate was blown dry after every single deposition step.

Figure 9:
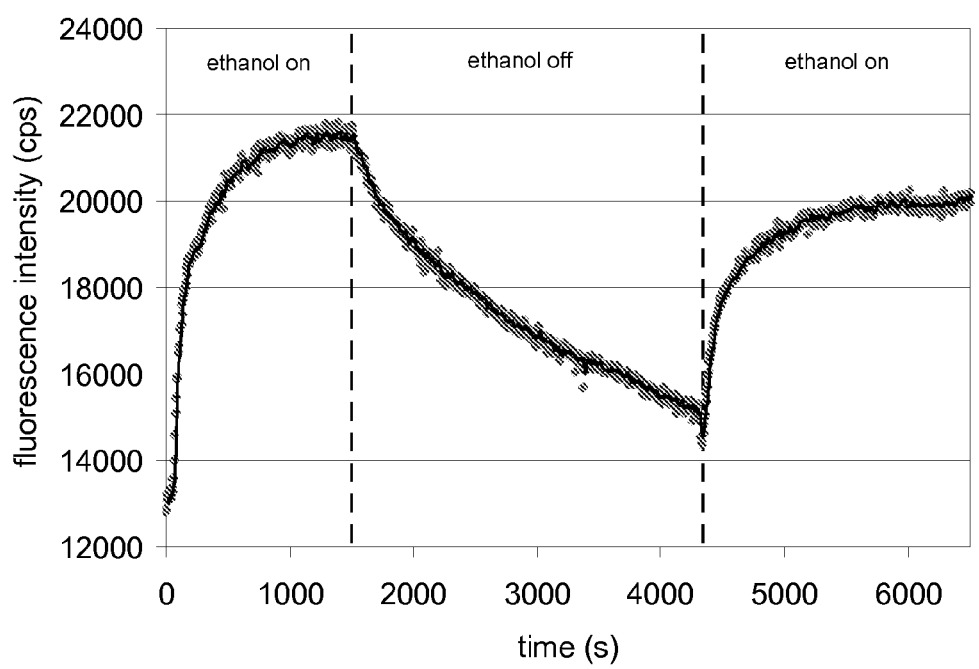
FIG. 9 shows the emission spectrum of the complete transducer stack after deposition on quartz substrates in the presence of ethanol vapour.

PL emission spectra (excitation wavelength 514 nm) of the substrate were measured in the presence of ethanol vapour. The ethanol vapour was obtained by bubbling $N_2$ through ethanol. The PL spectra were recorded using a confocal Raman microscopy set-up. The sample showed a clear response to ethanol as shown in FIG. 9.

This experiment shows that the entire stack can be successfully fabricated and that it shows a response to ethanol using a polyelectrolyte layer thickness of 10 nm.

Example 9

Fabrication and Photoluminescence of the Entire Stack

Quartz substrates were cleaned using piranha solution ($H_2SO_4/H_2O_2$ 3:1 v/v) and rinsed with water. After rinsing, a HMDS primer (hexamethyldisilazane) was applied to the substrates. Then, 1 nm of Au was sputtered on the substrates followed by annealing at 200° C. for 20 hours.

The next step was deposition of $Al_2O_3$ spacers using layer thicknesses of 6, 9, 12, 15 and 18 nm by sputter deposition. Finally, the substrates were immersed in the above described MAA-QD/PDADMAC solution for 30 minutes.

Figure 10:
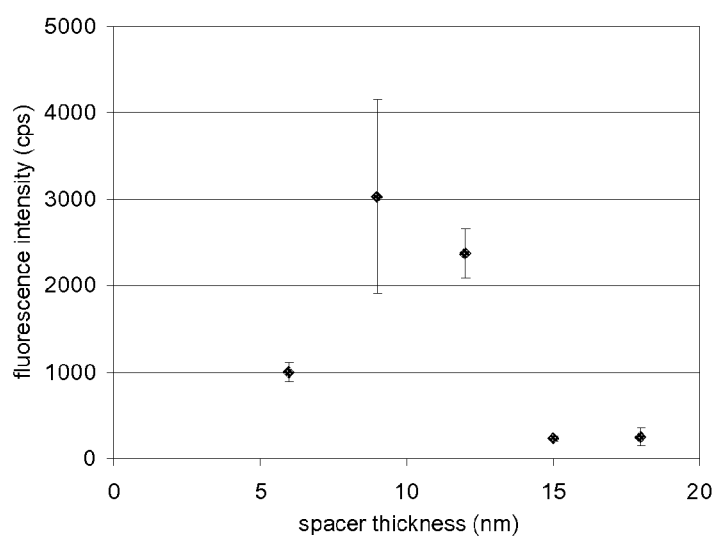
FIG. 10 shows the photoluminescence response of a gas sensor as a function of the thickness of the spacer layer.

PL emission spectra (excitation wavelength 514 nm) of the substrates were measured using a confocal Raman microscopy set-up. The samples showed a clear increase in PL for the $Al_2O_3$ spacer layer thickness of 9 nm as shown in FIG. 10.

This experiment shows that the entire stack can be successfully fabricated and that it shows the highest quantum dot luminescence using a spacer layer thickness around 9 nm.

The invention claimed is:

1. A gas sensing device comprising:
   a first layer and a second layer separated from each other by a gas absorption layer, said first and second layers electromagnetically interacting with each other upon illumination with light within a light frequency range, said gas absorption layer being configured for passing said electromagnetic interaction and having a variable thickness which changes upon absorption of a gas in such a way that said electromagnetic interaction is detectably affected, wherein
   (a) the first layer is a nanoparticle layer provided for generating a surface plasmon resonance within a plasmon resonance frequency range upon illumination with light within the light frequency range; and
   (b) the second layer is a quantum dot layer having an absorption spectrum overlapping with said plasmon resonance frequency range of said nanoparticle layer, said quantum dot layer showing photoluminescence in a photoluminescence emission frequency range upon absorption of energy within an absorption spectrum of said quantum dot layer;
   a light detector configured to detect photoluminescence of said quantum dot layer within said photoluminescence emission frequency spectrum; and
   a computer configured to determine a concentration of said gas in the vicinity of said gas absorption layer based at least in part on the detected photoluminescence of said quantum dot layer.
2. A gas sensing device according to claim 1, wherein the plasmon resonance frequency range at least partly overlaps with said photoluminescence emission frequency range.

3. A gas sensing device according to claim 1, wherein the nanoparticle layer shows a maximum plasmon resonance at a first frequency higher than a second frequency at which the quantum dot layer shows a maximum photoluminescence.

4. A gas sensing device according to claim 1, wherein said light emitting device is a light emitting diode in direct contact with said nanoparticle layer.

5. A gas sensing device according to claim 1, wherein said light detector is a photodiode in direct contact with said quantum dot layer.

6. A gas sensing device according to claim 1, wherein said nanoparticle layer comprises a material selected from the group consisting of Au, Ag, Cu, or any combinations thereof or core/shell particles, wherein the shell is selected from the group consisting of Au, Ag, Cu or any combination thereof.

7. A gas sensing device according to claim 1, wherein said quantum dot layer comprises a material selected from the group consisting of semiconductor nanocrystals made of II/VI compounds, such as CdSe, CdTe, CdS, ZnS, ZnSe, PbTe, PbSe, PbS, CdSe/ZnS or CdTe/ZnS, core/shell quatum dots, and combinations thereof; III/V compounds such as InAs, InP, InN, GaAs, GaN, and combinations thereof; and metal oxides, such as ZnO.

8. A gas sensing device according to claim 1, wherein said gas absorption layer comprises a material selected from the group consisting of poly($\gamma$-aminopropylethoxy/propylethoxysiloxane), poly($\gamma$-aminopropylethoxy/octadecylethoxysiloxane), poly(ethylene-vinyl acetate), polydimethylsiloxane, polyether-urethane, cynaopropylmethyldimethylsiloxane, poly(vinyl acetate), poly(iso-butyrene), polycarbonate urethane, conductive polymers, hydrogels, dendrimers, polyelectrolyte multilayers, such as poly(styrene sulfonate) (PSS)/poly(diallyldimethylammonium chloride) (PDADMAC).

9. A gas sensing device according to claim 1, wherein the thickness of said gas absorption layer before gas absorption is between 5 nm and 30 nm.

10. A gas sensing device according to claim 1, wherein the gas sensing device further comprises at least two electrodes, wherein a first electrode is in direct contact with the nanoparticle layer and a second electrode is in direct contact with the quantum dot layer.

11. A gas sensing system comprising a plurality of the gas sensing devices according to claim 1.

12. A gas sensing system according to claim 11, wherein at least two of said plurality of gas sensing devices comprise gas absorption layers with different thicknesses before absorption of the gas, wherein the gas absorption layers are made of at least one of a same material and a different material.

13. A gas sensing system according to claim 11, wherein at least two of said plurality of gas sensing devices comprise gas absorption layers made of different materials for absorption of different gases.

14. A method for fabricating a gas sensing device according to claim 1, the method comprising:
(a) providing a substrate;
(b) forming one of said nanoparticle layer and said quantum dot layer over said substrate;
(c) forming said gas absorption layer over said one layer; and
(d) forming the other of said nanoparticle layer and said quantum dot layer over said gas absorption layer.

15. The method according to claim 14, wherein said gas absorption layer is fabricated by a layer-by-layer polyelectrolyte deposition technique, where said layer-by-layer polyelectrolyte deposition technique comprises alternating a polycationic layer and a polyanionic layer.

16. A method comprising:
(a) providing a gas sensing device comprising:
a first layer and a second layer separated from each other by a gas absorption layer, said first and second layers electromagnetically interacting with each other upon illumination with light within a light frequency range, said gas absorption layer being configured for passing said electromagnetic interaction and having a variable thickness which changes upon absorption of a gas in such a way that said electromagnetic interaction is detectably affected, wherein
(i) the first layer is a nanoparticle layer provided for generating a surface plasmon resonance within a plasmon resonance frequency range upon illumination with light within the light frequency range; and
(ii) the second layer is a quantum dot layer having an absorption spectrum overlapping with said plasmon resonance frequency range of said nanoparticle layer, said quantum dot layer showing photoluminescence in a photoluminescence emission frequency range upon absorption of energy within an absorption spectrum of said quantum dot layer;
(b) illuminating said gas sensing device at a wavelength corresponding to a plasmon resonance frequency of said nanoparticle layer;
(c) detecting a first quantum dot luminescence signal;
(d) exposing said gas absorption layer to a gas;
(e) illuminating said gas sensing device at said wavelength corresponding to said plasmon resonance frequency of said nanoparticle layer;
(f) detecting a second quantum dot luminescence signal;
(g) calculating a difference between said first quantum dot luminescence signal and said second quantum dot luminescence signal; and
(h) calculating a gas concentration from said difference between said first quantum dot luminescence signal and said second quantum dot luminescence signal.

17. The method according to claim 16, wherein said nanoparticle layer is illuminated with a broad-band light source, and wherein a cut-off filter is used to prevent direct excitation of said quantum dot layer, the cut-off filter being placed between said broad-band light source and said nanoparticle layer.

18. A gas sensing device according to claim 1, wherein the thickness of the gas absorption layer increases upon absorption of a gas.

19. A gas sensing device according to claim 1, wherein the thickness of the gas absorption layer before gas absorption is selected such that before gas absorption the distance between the nanoparticle layer and the quantum dot layer is within a range between 70% and 150% of the optimum distance corresponding to a maximum intensity of the photoluminescence.

20. A gas sensing device according to claim 1, wherein the thickness of the gas absorption layer before gas absorption is selected such that before gas absorption the distance between the nanoparticle layer and the quantum dot layer is within a range between 90% and 110% of the optimum distance corresponding to a maximum intensity of the photoluminescence.

21. A gas sensing device according to claim 1, wherein determining a concentration of said gas in the vicinity of said gas absorption layer based at least in part on the detected photoluminescence of said quantum dot layer comprises:
calculating a difference between the detected photoluminescence of said quantum dot layer and a reference quantum dot luminescence signal, wherein the reference quantum dot luminescence signal is a reference signal detected prior to gas absorption; and calculating a gas concentration from said difference between the detected photoluminescence of said quantum dot layer and a reference quantum dot luminescence signal.

22. A gas sensing device according to claim 1, wherein the thickness of the gas absorption layer before gas absorption is selected such that before gas absorption the distance between the nanoparticle layer and the quantum dot layer is just beneath the optimum distance corresponding to a maximum intensity of the photoluminescence, so as to reduce a false positive, wherein upon absorption of gas, the thickness of the gas absorption layer changes such that the change in the thickness results first in a small increase of the detected photoluminescence, followed by a large decrease in the detected photoluminescence.

23. A gas sensing device according to claim 1, wherein the thickness of the gas absorption layer before gas absorption is selected such that before gas absorption the distance between the nanoparticle layer and the quantum dot layer is just above the optimum distance corresponding to a maximum intensity of the photoluminescence, so as to reduce a false positive.

* * * * *

UNITED STATES PATENT AND TRADEMARK OFFICE
CERTIFICATE OF CORRECTION

PATENT NO. : 8,525,129 B2
APPLICATION NO. : 12/743909
DATED : September 3, 2013
INVENTOR(S) : Offermans et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 370 days.

Signed and Sealed this
Fifteenth Day of September, 2015

Michelle K. Lee
*Director of the United States Patent and Trademark Office*